United States Patent [19]

Petrofsky et al.

[11] Patent Number: 4,480,830
[45] Date of Patent: Nov. 6, 1984

[54] METHOD AND APPARATUS FOR EXERCISING

[75] Inventors: Jerrold S. Petrofsky, Beavercreek; Roger M. Glaser, Dayton, both of Ohio; Steven H. Petrofsky, Florissant, Mo.; Harry H. Heaton, III, Beavercreek, Ohio

[73] Assignee: Wright State University, Dayton, Ohio

[21] Appl. No.: 417,935

[22] Filed: Sep. 14, 1982

[51] Int. Cl.³ .............................................. A63B 21/12
[52] U.S. Cl. .................................. 272/117; 128/25 R; 128/795; 128/423 W; 272/125; 272/134; 272/DIG. 5; 272/DIG. 6
[58] Field of Search ................... 272/117, 93, DIG. 6; 128/423 W, 733, 25 B, 25 R, 24.1, 796, 423 R, 80 G, 80 R, 795

[56] References Cited

U.S. PATENT DOCUMENTS

| | | | |
|---|---|---|---|
| 1,498,529 | 6/1924 | Allen | 128/796 |
| 2,630,115 | 3/1953 | Bierman | 128/25 B |
| 2,815,020 | 12/1957 | Barkschat | 128/25 B |
| 3,000,632 | 9/1961 | Fuchs | 262/117 |
| 3,083,712 | 4/1963 | Keegan, Jr. | 128/419 |
| 3,204,637 | 9/1965 | Frank et al. | 128/423 |
| 3,344,792 | 10/1967 | Offner et al. | 128/419 |
| 3,387,147 | 6/1968 | Radwan | 307/275 |
| 3,628,538 | 12/1971 | Vincent et al. | 128/422 |
| 3,817,254 | 6/1974 | Maurer | 128/421 |
| 3,848,467 | 11/1974 | Flavell | 272/129 |
| 3,911,910 | 10/1975 | Oesau | 128/82.1 |
| 3,929,335 | 12/1975 | Malick | 272/57 |
| 3,989,240 | 11/1976 | Victor et al. | 272/125 |
| 4,071,033 | 1/1978 | Nawracaj et al. | 128/420 |
| 4,148,321 | 4/1979 | Wyss et al. | 128/420 |
| 4,165,750 | 8/1979 | Aleev et al. | 128/422 |
| 4,177,819 | 12/1979 | Kofsky et al. | 128/422 |
| 4,257,590 | 3/1981 | Sullivan | 272/117 |
| 4,284,157 | 8/1981 | Lay | 180/65 |
| 4,333,340 | 6/1982 | Elmeskog | 73/379 |
| 4,392,496 | 7/1983 | Stanton | 128/423 W |

FOREIGN PATENT DOCUMENTS

3030897 3/1982 Fed. Rep. of Germany .
2052994 2/1981 United Kingdom .
635935 10/1978 U.S.S.R. .
719635 5/1980 U.S.S.R. .

OTHER PUBLICATIONS

Clinical Electrical Stimulation, by G. Keith Stillwell—(Name of publication unknown)—(pp. 114–117), (Date Unknown).
Microprocessor Controlled Stimulation in Paralyzed Muscle, Petrofsky & Phillips, IEEE NAECON Record, (6/79), 198–210.
Muscle Fiber Recruitment and Blood Pressure Response to Isometric Exercise, Petrofsky et al., J. Appl. Physiol.: 50(1), 32–37, 2/81.
Control of the Recruitment and Firing Frequencies of Motor Unit in Electrically Stimulated Muscles in the Cat, Petrofsky, Med. Biol. Eng. & Comput., 5/78, 16, 302–308.

(List continued on next page.)

Primary Examiner—Richard C. Pinkham
Assistant Examiner—Leo P. Picard
Attorney, Agent, or Firm—Biebel, French & Nauman

[57] ABSTRACT

An exercising method and apparatus for use in the treatment of paralyzed muscles. The method and apparatus make use of a set of transcutaneous electrodes which are placed upon the skin of the subject over muscles which are to be stimulated. A computer controlled stimulator generates a pair of alternately pulsed stimulation signals which are applied across different pairs of stimulation electrodes to produce controlled muscle contraction. Muscle movement is resisted by a dynamic load, and a position sensor provides a feedback signal indicating the movement actually achieved. The computer uses the feedback signal for modifying the control signal applied to the stimulator. The exercise routine is disclosed as being conducted upon the leg of a subject seated in a specially designed exercise chair.

12 Claims, 8 Drawing Figures

OTHER PUBLICATIONS

Sequential Motor Unit Stimulation through Peripheral Motor Nerves in the Cat, Petrofsky, Med. & Biol. Eng. & Comput., 1/79, 087–093.

The 81. of Temperature, Initial Length and Electrical Activity on the Force–Velocity Relationship of the Medial Gastrocnemius Muscle of the Cat, Petrofsky and Phillips, J. Biomechanics, vol. 14, No. 5, 297–306, 2/1981.

Constant-Velocity Contractions in Skeletal Muscle by Sequential Stimulation of Muscle Efferents, Petrofsky and Phillips, Med. & Biol. Eng. & Comput., 9/79, 17, pp. 583–592.

Impact of Recruitment Order on Electrode Design for Neural Prosthetics of Skeletal Muscle, Petrofsky and Phillips, Am. J. Phys. Med., vol. 60, 4/81, pp. 243–253.

New Microcomputer May Someday Bring Paralyzed Limbs to Life, The Washington Post, Feb. 16, 1961 by Philip J. Hilts.

Walking Sway from Paralysis, Denise Grady, Discover Magazine, May 1981, pp. 26–28 and 30.

Control of Contraction Strength of Electrically Stimulated Muscle by Pulse Width and Frequency Modulation, Peckham, Proc. 29th ACEMB, p. 116, Nov. 6–10, 1976.

The Effects of Length and Stimulus Rate on Tension in the Isometric Cat Soleus Muscle, Rack and Westbury, J. Physiol., (4/69), 204, pp. 443–460.

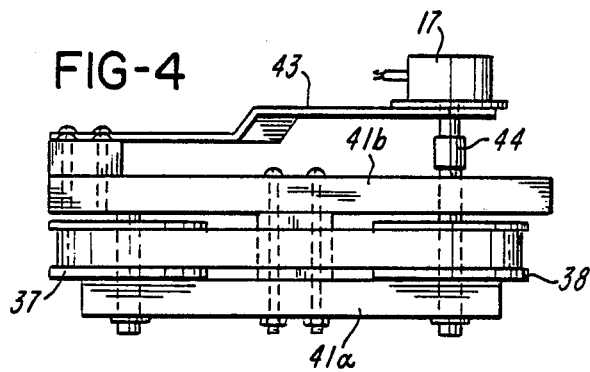
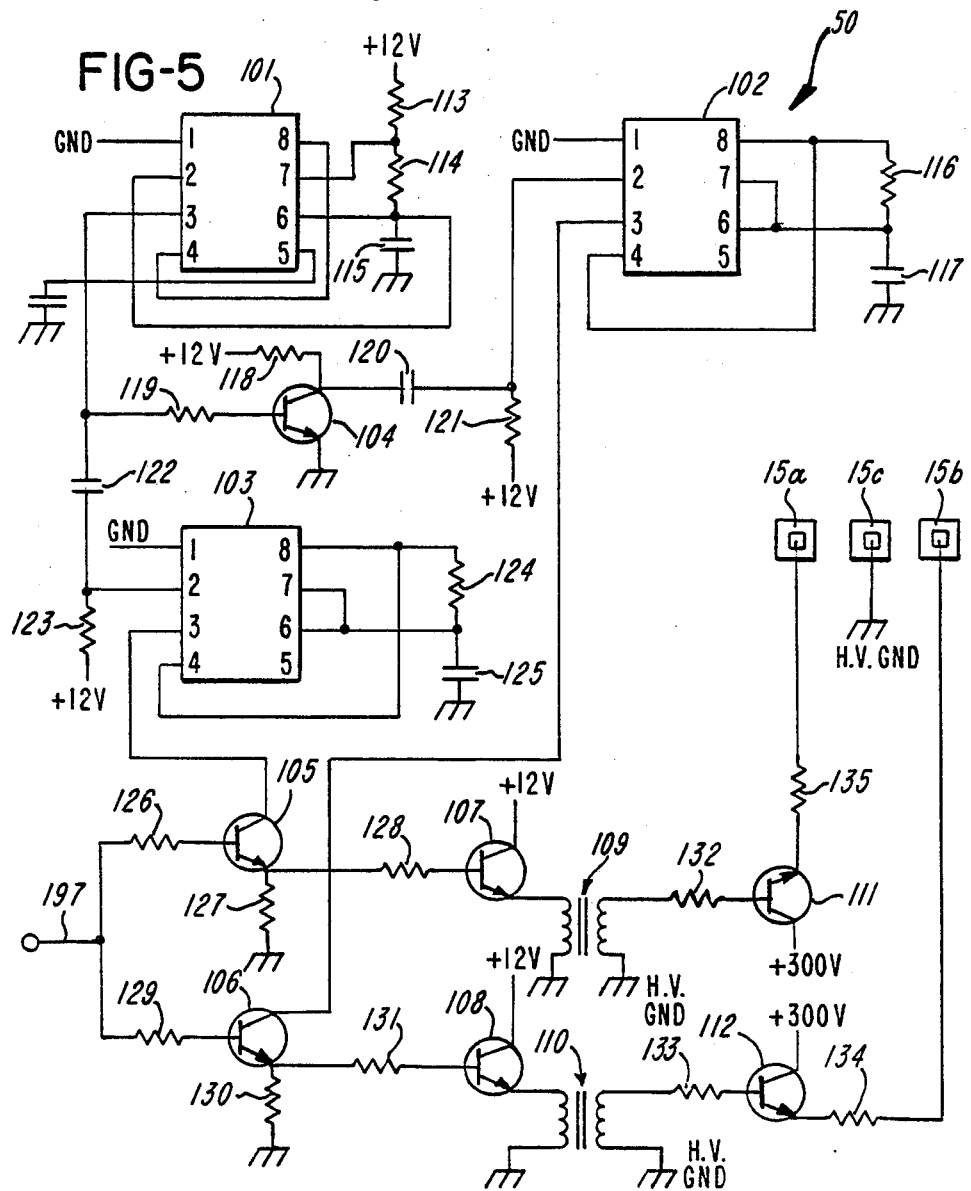

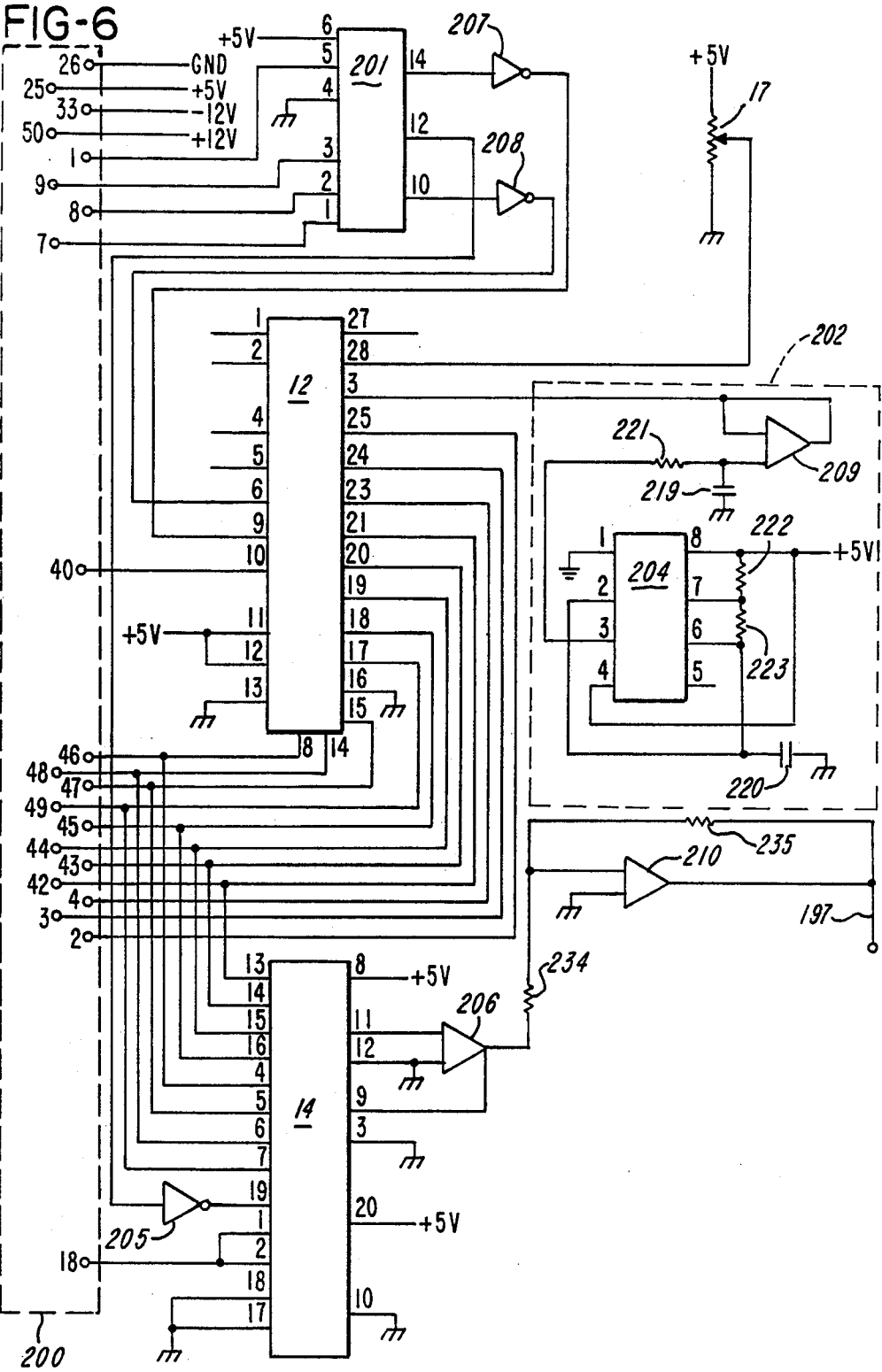

METHOD AND APPARATUS FOR EXERCISING

BACKGROUND OF THE INVENTION

The present invention relates to a method and apparatus for exercising and, more particularly, to a computer controlled method and apparatus for monitoring muscular activity and adjusting an electrical stimulus to provide controlled and sustained isokinetic contractions. Still more particularly the present invention relates to a method and apparatus for directing coordinated movement of several muscles and exercising them through a specific exercise routine having therapeutic applications in the treatment of paralysis.

The invention which is disclosed and claimed herein has particular value in the treatment of persons who have suffered injuries resulting in spinal cord damage. This particular type of damage often times produces partial or total paralysis of muscles which are controlled from a point below the point of spinal cord damage. The victim then faces a life of relative inactivity and deterioration of muscles which otherwise would be active. It has now been found in accordance with this invention that such muscles can be stimulated to engage in an exercise program once thought to be impossible. Moreover, it has been found that such an exercise program can restore normal muscle tone, even after years of inactivity.

Since the work of Galvani in 1791, it has been known that electricity can be used to induce muscle contractions. Recently, there has been increased awareness of the value of electrostimulation in muscle therapy.

Numerous devices and techniques have been developed for supplying electrical pulses as part of a therapeutic regime of muscle stimulation. Several examples of these are found in the patent literature. Radwan, U.S. Pat. No. 3,387,147 (1968) discloses a muscle stimulating pulse generator designed to provide a pulse signal having a relatively high voltage-to-width ratio and a steep rising wavefront.

Maurer, U.S. Pat. No. 3,817,254 (1974), discloses a transcutaneous stimulator for use in suppressing pain designed to differentially stimulate touch versus pain nerve fibers in an effort to reduce the prickly sensation known to accompany some pain therapy. Maurer notes that differences in the response of nerves to electrostimulation can be used to selectively stimulate different types of nerves. According to Maurer, nerve fibers are distinguished in terms of their size and conduction velocity. He notes that the amplitude of electrical stimulation required to elicit a muscle response increases as the fiber size decreases.

Nawracaj et al, U.S. Pat. No. 4,071,033 (1978), discloses an electrostimulation device which utilizes a heterodyne effect to produce an otherwise painful low frequency stimulus in a muscle and cause the muscle to contract and relax at a low frequency.

Wyss et al, U.S. Pat. No. 4,148,321 (1979), discloses a muscular therapy similar in some respects to Nawracaj et al wherein muscles are made to rhythmically contract and relax at a very low frequency which is induced by modulating a medium frequency current between 3,000 and 100,000 Hz with a low frequency current less than 1 Hz. In one embodiment Wyss et al uses a phase shifter to transform the modulated output current into a three phase current, which is delivered to three electrodes angularly spaced about a limb to provide deep uniform stimulation.

Kofskey et al, U.S. Pat. No. 4,177,819 (1979), teaches an apparatus for stimulating a muscle for 2 to 20 seconds at 2 to 50 second intervals using a 2000 to 3000 Hz signal modulated at 40 to 50 Hz. In one embodiment, the muscle stimulating waveform is controlled by a microprocessor which gradually increases and decreases the amplitude of the stimulation at the beginning and end of each pulse. The microprocessor responds to signals from a no-load/overload sensor and to a manually controlled gain setting signal.

It can be seen that the efforts embodied in the foregoing patents focus on the stimulus itself as the therapeutic agent and have as a principal objective to optimize the intensity, duration and frequency of the stimulus to enhance its therapeutic effects. In the disclosed therapies, the muscle is not stimulated against a load. These prior art systems do not provide smooth isometric contractions and do not respond to muscle activity response to muscle activity in these prior systems.

In order to train a muscle and make it physically strong, it is necessary to work the muscle against a load while producing powerful, sustained, isokinetic contractions at a substantial proportion of the muscle's strength. Isokinetic contractions cannot be maintained for prolonged periods of time in the aforementioned therapies, because they stimulate the muscle synchronously using frequencies much higher than normal physiological frequencies. This causes the muscle to fatigue rapidly, making it impossible to maintain muscle tension.

Petrofsky, "Microprocessor Controlled Stimulation in Paralyzed Muscle", IEEE August 1979 outlines a computer-controlled stimulation system which minics normal asynchronous recruitment of motor units and firing rate control in the gastrocnemius muscle of a cat. A computer was programmed to set the recruitment order of the motor units as it sensed fatigue in the muscle. This was accomplished by using an anodal block electrode in combination with a sequential electrode sleeve. The electrode sleeve was placed around the motor nerve to the muscle and was configured for alternately stimulating three groups of neurons in the nerve. The anodal block electrode was placed just proximal to the muscle. Muscle fatigue was sensed by a strain gauge transducer mounted on a bar attached to one end of the muscle.

The Petrofsky article teaches that electrostimulation can be controlled by a microprocessor in such a way as to develop isometric contractions in a muscle. However, there is no teaching of any method or apparatus for causing smooth, natural isokinetic contractions. Also, the techniques taught by Petrofsky are not applied to man.

SUMMARY OF THE INVENTION

It is an object of the present invention to provide a method and apparatus for electrically stimulating a muscle and exercising the muscle through a specific exercise routine based upon feedback control.

It is another object of this invention to provide apparatus and method for stimulating a human muscle to contract against a dynamic load.

It is still another object of the invention to provide improved apparatus and method for stimulating contraction of a human muscle.

These and other objects of the present invention are accomplished through use of a stimulation device which generates a pair of stimulation signals comprising alternately generated pulses of stimulation energy. The stimulation signals are applied across pairs of electrodes which are preferably adhered to the skin immediately above a muscle to be stimulated.

In the preferred embodiment the stimulation apparatus is controlled through a digital to analog converter by a digitally controlled microprocessor. The limb which is moved by the stimulated muscle is secured against a dynamic load which yieldingly resists movement of the muscle. A feedback sensor senses the movement actually achieved by the limb and transmits an indication thereof through an analog to digital converter back to the microprocessor.

In an exercise routine according to the present invention, a plurality of transcutaneous stimulators are applied to the skin of the subject in a pattern for stimulating a muscle which is connected for moving the limb to be exercised. The stimulators are then excited by a plurality of stimulation signals having profiles for causing the muscle to contract and produce a predetermined movement of the limb. While the limb is contracting, a resisting force is applied thereagainst to cause exertion of the muscle during its contraction. The movement of the limb is sensed and a corresponding feedback signal is generated. The feedback signal is monitored to determine when a predetermined movement has been achieved. After the predetermined movement has been achieved, the stimulation signals are altered to permit the limb to return to its initial position. The process is the repeated to produce an exercise routine.

BRIEF DESCRIPTION OF THE DRAWINGS

FIG. 4 is a view taken along line 4—4 of FIG. 2;

FIG. 5 is a schematic illustration of a stimulation apparatus;

FIG. 6 is a schematic illustration of a control system for the stimulation apparatus of FIG. 5;

DESCRIPTION OF THE PREFERRED EMBODIMENT

Figure 1:
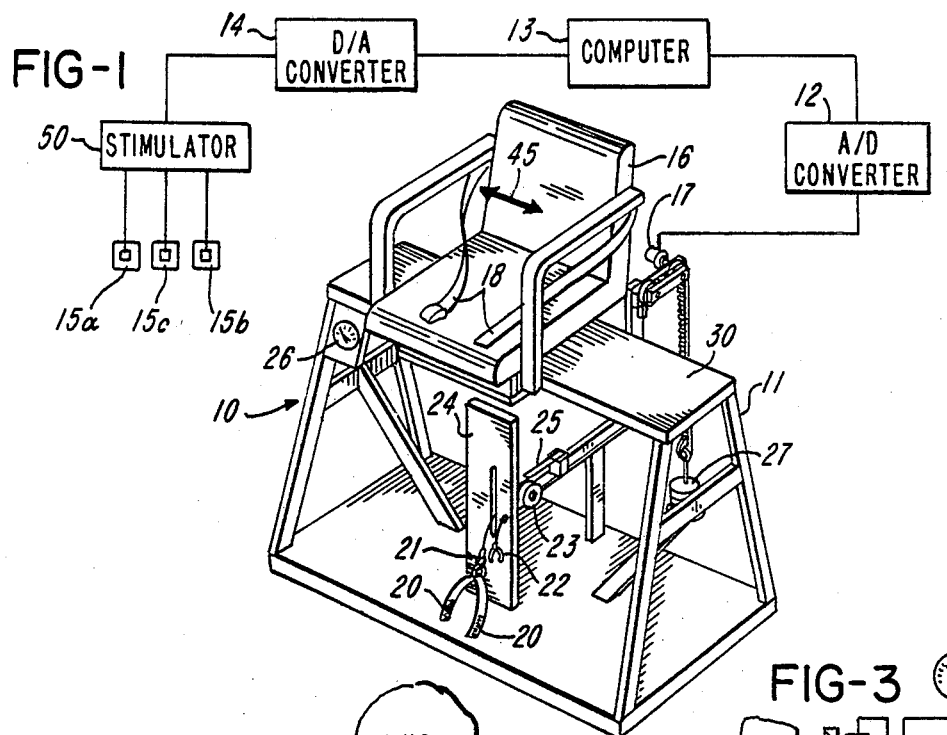
FIG. 1 is a schematic illustration of exercising apparatus in accordance with the present invention.
Figure 2:
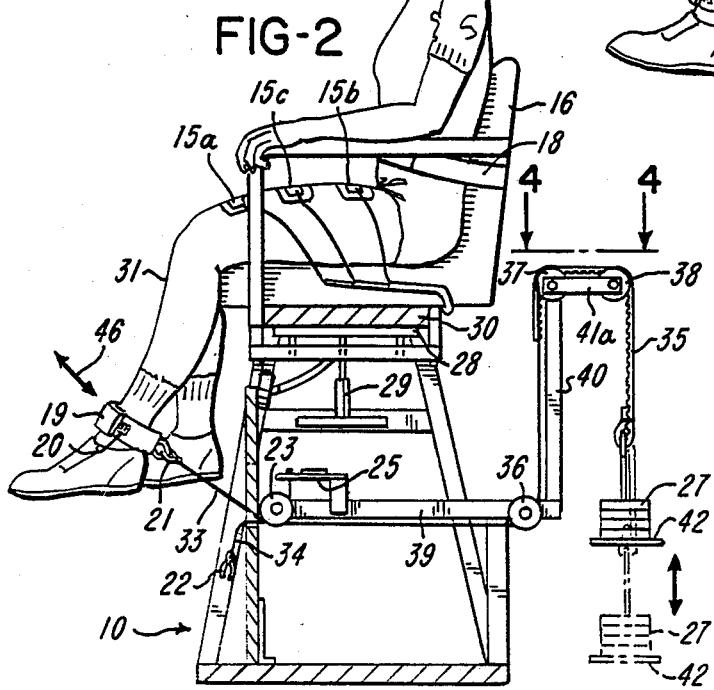
FIG. 2 is a side elevation view of an exercise chair.

FIG. 1 illustrates an exercise system 10 constructed in accordance with this invention. The exercise system may comprise a chair 16 mounted on a support frame 11. Chair 16 rests upon a support board 30 and is clamped in place by a clamp plate 28, as illustrated in FIG. 2. Clamp plate 28 may be forced upwardly against the lower surface of support board 30 by any convenient means, such as, for instance, a rotary handle and screw arrangement 29. When clamp 28 is released chair 16 may be moved along the surface of support board 30 as illustrated by the arrow 45. This enables positioning of chair 16 for accommodating an exercise routine for either the left leg or the right leg of a person seated in chair 16.

Exercise system 10 also comprises a seat belt 18 for securing a person in chair 16 and a leg strap 19 for grasping the lower portion of a leg 31. Leg strap 19 is provided with interlocking pieces of hook and loop fastening fabric 20, 20 of the type sold by Velcro U.S.A., Inc. of New York, New York under the trademark VELCRO. Thus leg strap 19 be easily and securely fastened around a leg of any size.

Leg strap 19 has a steel eyelet for fastening to one or the other of a pair of scissor-type eyelet fasteners 21, 22. Fasteners 21 and 22 are attached to pair of cables 33, 34, respectively, which extend through a facing board 24.

Figure 3:
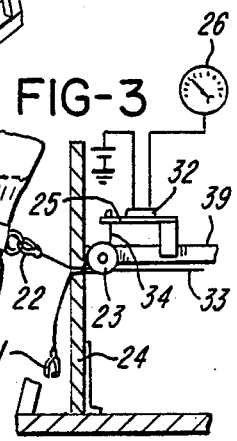
FIG. 3 is an illustration of means for indicating the isometric load developed by a human leg.

Cables 33 and 34 are guided by a roller 23 having a pair of offset guide channels (not illustrated). Cable 33 extends rearwardly from roller 23 around a roller 36 and thence upwardly for attachment to a toothed belt 35. Cable 34 wraps around roller 23 and extends upwardly for attachment to a relatively stiff bending arm 25 supported upon frame member 39, as best illustrated in FIG. 3.

Toothed belt 35 extends around a pair of toothed rollers 37 and 38 mounted between a pair of support plates 41a and 41b, as best illustrated in FIG. 4. Support plates 41a and 41b are securely supported by frame member 40, which in turn is supported by frame member 39.

Belt 35 supports a set of weights placed upon a pan 42. Thus when the leg 31 moves arcuately as indicated by arrow 46, the weights 27 are raised or lowered. The arrangement provides a dynamic load which resists but does not prevent movement of leg 31.

When the leg 31 is extended upwardly, pulling cable 33 and belt 35, the movement is measured by a potentiometer 17 (see FIG. 4) attached to roller 38 by a coupling device 44. The housing for potentiometer 17 is supported by a support arm 43 secured to the upper support plate 41, as viewed in FIG. 4.

As the leg 31 moves and pulls belt 35 across roller 38, the potentiometer 17 transmits a feedback signal to A/D converter 12. A/D converter 12 converts the feedback signal into a digital format for processing by computer 13, as hereinafter described in detail. Computer 13 responds to the feedback signal by transmitting a digital control signal to D/A converter 14. D/A converter 14 then generates an analog stimulation signal for stimulator 50. Stimulator 50 uses the control signal from D/A converter 14 for generation of a pair of stimulation signals which are applied across electrodes 15a, 15b and 15c. Electrodes 15a, 15b and 15c are commercially available transcutaneous electrodes such as MEDTRONIC Model 3793 electrodes sold by Medtronic, Inc. of Minneapolis, Minn.

For an exercise as hereinafter described the electrodes are placed in spaced positions above the quadriceps muscles of one leg, as generally illustrated in FIG. 2. The electrodes are attached to the leg of the subject by hypoallergenic tape or elastic bandages. Prior to application of the electrodes, the skin is cleaned and dried. An electrode gel, such as TENS electrode gel, also sold by Medtronic, Inc. is applied to the electrodes before thay are placed upon the skin of the subject.

When the stimulation signals from stimulator 50 are applied to electrodes 15a, 15b and 15c the quadriceps muscles of the subject are stimulated to contract and raise the leg 31 against the dynamic resistance of cable 33 as described above. Alternatively, leg strap 19 may be connected to cable 34 in which case leg 31 strains isometrically against bending arm 25. This produces an output signal from a strain gauge 32 mounted on top of bending arm 25. Strain gauge 32 is connected to provide a load signal for a meter 26 which may be mounted at any convenient location. The meter 26 provides a "strength" indication for use in the exercise procedure hereinafter described in detail.

Figure 7:
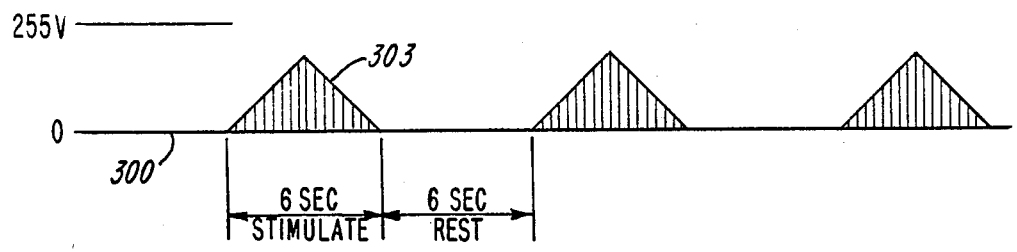
FIG. 7 is a schematic illustration of a stimulation signal.
Figure 8:
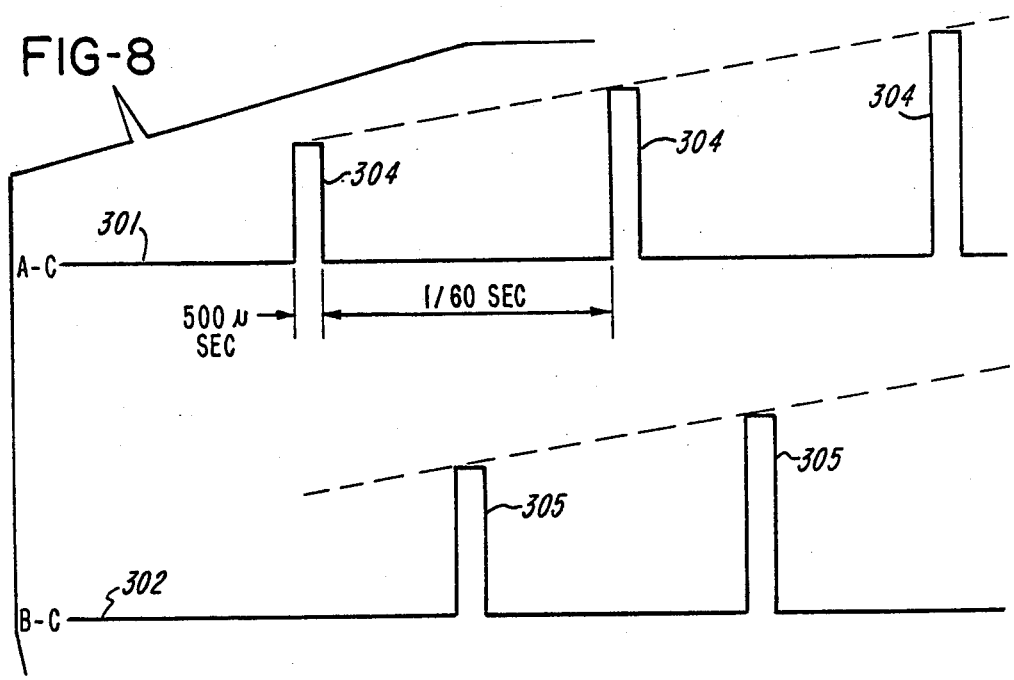
FIG. 8 is an enlarged schematic illustration of portions of two alternately pulsed stimulation signals.

The stimulation signals which are applied to electrodes 15a, 15b, and 15c are illustrated in FIGS. 7 and 8. Stimulator 50 generates a first signal 301 as illustrated by the top line of FIG. 8 and a second signal 302 as illustrated by the bottom line of FIG. 8. Signal 301 is applied across terminals 15a and 15c, while signal 302 is applied terminals 15b and 15c. Terminal 15c is connected to high voltage ground, as hereinafter described with reference to FIG. 5.

Each of signals 301 and 302 has an envelope generally illustrated by triangular projections 303 rising above the line 300 of FIG. 7. The signal is characterized by alternating stimulation and rest periods of approximately 6 seconds each. During the stimulation period the signal is pulsed at a frequency in a range from about 55 to 65 Hz and preferably about 60 Hz. The pulses which are so generated have peak values which increase gradually from a value near 0 volts to a maximum which is somewhat less than 255 volts and which produces maximum effort from the muscle or muscle group being stimulated. Thereafter the pulse amplitudes decrease gradually to a value near zero, and the muscle is rested. The maximum voltage value depends upon the state of exhaustion of the muscle and the effort which is desired. As the muscle tires, more stimulation voltage is required for production of the same effort. Generally speaking a maximum voltage of about 255 volts produces recruitment of all motor units and results in maximum effort by the muscle.

As shown in FIG. 8, signal 301 comprises a series of pulses 304 while signal 302 comprises another series of pulses 305. Pulses 304 and 305 are generated in an alternating sequence at a frequency of 60 Hz each. Thus the effective combined frequency is 120 Hz. Pulses 304 and 305 have peak values which conform with the signal envelope of FIG. 7. They have a duration of approximately 500 microseconds, so that each of signals 301 and 302 has a duty cycle of 0.03. It has been found that if the pulse width is increased, then the stimulation voltage may be decreased and vice versa.

The circuitry for producing signals 301 and 302 is illustrated in FIG. 5. The associated feedback and control circuitry is illustrated schematically in FIG. 6. The circuitry includes integrated circuits as identified in Table I and components as identified in Table II. Table III lists significant pin number designations for the principal integrated circuits listed in Table I.

TABLE I

| | Integrated Circuits |
|---|---|
| Ref. Numeral | Circuit Type |
| 12 | ADC0808 (National Semiconductor) |
| 13 | DAC0831 (National Semiconductor) |
| 101 | SE/NE 555 (Signetics) |
| 102 | SE/NE 555 (Signetics) |
| 103 | SE/NE 555 (Signetics) |
| 201 | SN74LS138 (Texas Instruments) |
| 204 | SE/NE 555 (Signetics) |
| 205 | 1/6 7404 |
| 206 | ½ LM1458 |
| 207 | 1/6 7404 |
| 208 | 1/6 7404 |
| 209 | ½ LM1458 |
| 210 | ½ LM1458 |
| 211 | ½ LM1458 |
| 212 | ½ LM1458 |
| 213 | ½ LM1458 |

TABLE I-continued

| | Integrated Circuits |
|---|---|
| Ref. Numeral | Circuit Type |
| 214 | ½ LM1458 |

TABLE II

| | Components |
|---|---|
| Ref. Numeral | Identification |
| 104 | 2N3904 |
| 105 | 2N3904 |
| 106 | 2N3904 |
| 107 | 2N3904 |
| 108 | 2N3904 |
| 111 | 2SC1308 |
| 112 | 2SC1308 |
| 113 | 100 k |
| 114 | 100 k |
| 115 | 0.1 μf |
| 116 | 10 k |
| 117 | 0.1 μf |
| 118 | 10 k |
| 119 | 10 k |
| 120 | 0.001 μf |
| 121 | 22 k |
| 122 | 0.001 μf |
| 123 | 22 k |
| 124 | 10 k |
| 125 | 0.1 μf |
| 126 | 470Ω |
| 127 | 10 k |
| 128 | 470Ω |
| 129 | 470Ω |
| 130 | 10 k |
| 131 | 470Ω |
| 132 | 1 k |
| 133 | 1 k |
| 134 | 100Ω |
| 135 | 100Ω |
| 136 | 0.1 μf |
| 219 | 39 μf |
| 220 | 10 μf |
| 221 | 100 k |
| 222 | 330 k |
| 223 | 680 k |
| 234 | 100 k |
| 235 | 82 k |

TABLE III

| | Pin Functions | | |
|---|---|---|---|
| Component | Pin No | Function Name | Function |
| Slot #3 of Apple Computer | 1 | I/O SELECT | LO during slot #3 addressing |
| | 2 | A0 | Address bit 0 |
| | 3 | A1 | Address bit 1 |
| | 4 | A2 | Address bit 2 |
| | 7 | A5 | Address bit 5 |
| | 8 | A6 | Address bit 6 |
| | 9 | A7 | Address bit 7 |
| | 18 | R/W | Buffered Read/Write signal |
| | 25 | +5 V | +5 volts |
| | 26 | GND | ground |
| | 33 | −12 v | −12 volts |
| | 40 | O | phase 0 clock |
| | 42 | D7 | Data bit 7 |
| | 43 | D6 | Data bit 6 |
| | 44 | D5 | Data bit 5 |
| | 45 | D4 | Data bit 4 |
| | 46 | D3 | Data bit 3 |
| | 47 | D2 | Data bit 2 |
| | 48 | D1 | Data bit 1 |
| | 49 | D0 | Data bit 0 |
| | 50 | +12 v | +12 volts |
| SN74LS138 | 1 | A | select line |
| | 2 | B | select line |
| | 3 | C | select line |
| | 4 | G2A | enable line |

TABLE III-continued

| Component | Pin No | Function Name | Function |
|---|---|---|---|
| | 5 | G2B | enable line |
| | 6 | G1 | enable line |
| | 10 | Y5 | output line |
| | 12 | Y3 | output line |
| | 14 | Y1 | output line |
| ADC 0808 | 3 | In5 | analog input #5 |
| | 6 | start | start strobe |
| | 8 | D3 | Data bit 3 |
| | 9 | out enable | output enable |
| | 10 | clock | clock |
| | 14 | D1 | data bit 1 |
| | 15 | D2 | data bit 2 |
| | 17 | D0 | data bit 0 |
| | 18 | D4 | data bit 4 |
| | 19 | D5 | data bit 5 |
| | 20 | D6 | data bit 6 |
| | 21 | D7 | data bit 7 |
| | 23 | Add C | address bit C |
| | 24 | Add B | address bit B |
| | 25 | Add A | Address bit A |
| | 27 | In 1 | analog input #1 |
| | 28 | In 2 | analog input #2 |
| DAC 0831 | 1 | CS | input latch |
| | 2 | $WR_1$ | data load |
| | 4 | $DI_3$ | digital input bit 3 |
| | 5 | $DI_2$ | digital input bit 2 |
| | 6 | $DI_1$ | digital input bit 1 |
| | 7 | $DI_0$ | digital input bit 0 |
| | 9 | $R_{fb}$ | zero adjustment |
| | 11 | $I_{out}\ 1$ | output proportional to digital input |
| | 12 | $I_{out}\ 2$ | output proportional to complement of digital input |
| | 13 | $DI_7$ | digital input bit 7 |
| | 14 | $DI_6$ | digital input bit 6 |
| | 15 | $DI_5$ | digital input bit 5 |
| | 16 | $DI_4$ | digital input bit 4 |
| | 19 | $I_{LE}$ | chip select |

The operation of stimulator 50 will now be described with reference to FIG. 5. That figure shows 3 integrated circuits 101, 102, and 103 of identical construction. These are timing circuits such as Signetics 555 timers. IC 101 is connected to operate as a 60 Hz free running multivibrator. The output from IC 101 is applied via transistor 104 to input pins 2 of IC 102 and 103. IC 102 and 103 produce alternating 500 microsecond pulses each at a frequency of 60 Hz for application to the collector terminals of transistors 105 and 106. The pulse width is set by appropriate selection of the resistance for resistors R116 and R124 and the capacitance of capacitors 117 and 125, as shown in the manufacturer's data sheets for integrated circuits 102 and 103. The phase between the pulses produced by integrated circuits 102 and 103 is set by appropriate selection of the resistance for resistors 113 and 114.

An analog voltage representing the desired envelope for the stimulation pulses is applied to input line 197, which is connected to the base terminals of transistors 105 and 106. Concomitantly, output pulses from pin 3 of IC 102 and pin 3 of IC 103 are applied to the collectors of transistors 106 and 105 respectively. As a result thereof transistors 106 and 105 generate emitter currents across resistors 130 and 127 providing voltage profiles of the general shape illustrated in FIGS. 7 and 8. These voltages are applied to the base terminals of transistors 108 and 107. This results in corresponding voltage pulses ranging between 0 and 12 volts across the primary windings of transformers 110 and 109.

The voltage pulses across the primary windings of transformers 110 and 109 produce low current, high voltage pulses ranging from 0 to 255 volts across the secondary windings of transformers 110 and 109. The secondary windings of transformers 110 and 109 have one side grounded to a high voltage ground which is different from the ground utilized for the primary windings thereof. The output pulses from the secondary windings are thereby RF isolated to maintain the safety of the person who is the subject of the exercise procedure.

Output voltage pulses from transformers 110 and 109 are applied to the base terminals of transistors 112 and 111 respectively. Transistors 112 and 111 provide a current gain so as to have high current, high voltage and low duty cycle pulses available for application across terminal pairs 15a–15c and 15b–15c. The analog driving signal appearing at line 197 is generated by the control system circuitry as illustrated in FIG. 6.

The heart of the control system is the computer 13, which in the embodiment described herein is an APPLE II computer sold by Apple Computer Inc. of Cupertino, Cal. The APPLE II computer is provided with several slots into which may be plugged connectors for customized peripheral devices. The system described herein is plugged into slot number 3, which includes a connector 200 as illustrated by dotted lines in FIG. 6. The computer addresses analog to digital converter 12 and digital to analog computer 13 through a decoder/demultiplexer 201. The peripheral board is addressed by the computer in memory locations C100 to C1FF (hexadecimal notation). Pin number 1 of connector 200 provides a signal from the computer's input-/output select line. This line becomes active whenever one of the memory locations C1FF to C100 are selected for memory read or write operations. Pin number 1 is tied to pin number 5 of IC 201, an SN74LS138 integrated circuit. Pin number 5 is the G2 input of IC 201. A signal at this terminal enables IC 201 to decode the three high order bits (A7, A6, and A5) of an eight-bit address provided by the computer. These three bits appear at pin numbers 9, 8 and 7 respectively of connector 200.

IC 201 is designed for producing eight decoded outputs, but only three of these outputs are used. These outputs appear at pin numbers 14, 12 and 10 and respectively read A/D converter 12, strobe D/A converter 14 and strobe A/D converter 12. A/D converter 12 is an eight channel device sold by National Semiconductor under the designation ADC0808. A/D converter 12 receives its clock from the system clock on pin number 40 of connector 200.

When a strobe signal appears at pin number 12 of IC 201, A/D converter 12 is enabled for reading and digitizing analog signals appearing at any one of eight analog input ports (only two of which are used). The two analog input ports are addressed by a three-bit address appearing at pin numbers 25, 24 and 23 of A/D converter 12. The three address bits are the three least significant bits of an eight-bit address generated by computer 13. These three bits appear at pin numbers 2, 3 and 4 of connector 200 (the three most significant bits appearing at pin numbers 7, 8 and 9 as above stated) and bit numbers 3 and 4 not being utilized.

Computer 13 generates the above mentioned eight-bit address whenever any one of computer memory address locations 50080 to 50087 (decimal notation) are strobed. Such strobing not only generates an associated eight-bit address, but also enables A/D converter 12 by causing generation of a strobe signal at output pin 12 of IC201, as above described. Memory locations 50080 to 50087 are strobed by execution of a "POKE" instruction, such as, for instance, the instruction "POKE 50080,0" appearing at line number 1450 of the computer program set forth in TABLE IV hereof.

As mentioned above, the described embodiment supplies only two analog input signals for digitizing by A/D converter 12. These two signals appear at pin numbers 3 and 28 of A/D converter 12 and are addressed respectively by "POKING" memory locations 50080 and 50082 respectively. The resulting digitized representation thereof appears in eight-bit format at pin numbers 17, 14, 15, 8, 18, 19, 20 and 21 of A/D converter 12. These eight bits are read into memory location 49952 (decimal notation) upon execution of a "PEEK" instruction.

It is therefore seen that when memory addresses 50080 through 50087 are strobed, the computer selects the analog channel which is to be multiplexed into A/D converter 12. Simultaneously with this selection A/D converter 12 is strobed to start conversion of the analog signal to digital format. A maximum of 100 microseconds is required for the analog to digital conversion, after which the computer may execute a normal memory read cycle, whereby the digitized data is transferred onto the data bus and stored in memory location 49952. It is to be noted that the output of A/D converter 12 is a eight-bit binary signal ranging between values of 0 and 255 (decimal) for analog input voltages between 0 and 5 volts.

The analog signal supplied to pin No. 3 of A/D converter 12 has a triangular voltage profile and is produced by a profile generating circuit 202, comprising IC 204, amplifier 209, capacitors 219 and 220, and resistors 219 through 223. IC 204 generates a square wave at 1/6 Hz which is converted to a triangular ramp by capacitor 219 and resistor 221 and is buffered by amplifier 209. The triangular voltage profile, so generated, represents a desired response from potentiometer 17 when the leg of the subject is being stimulated to raise and lower.

The output of potentiometer 17 is applied to pin No. 28 of A/D converter 12, as shown in FIG. 6. An output of 5 volts from potentiometer 17 represents a shaft angle rotation of 360°. The diameter of roller 38 is selected such that one rotation thereof corresponds to a leg movement of about 70 degrees from its initial vertial position.

The amplitude of the analog stimulation signal appearing at line 197 is controlled by D/A converter 14, a DAC0831 integrated circuit sold by National Semiconductor. D/A converter 14 is selected for operation by applying a strobe signal to pin 19 thereof. Also, a write signal (logic LO) is applied to input terminals 1 and 2 for activating the transfer of data to the internal latch register of D/A converter 14. The data so transferred is an eight-bit stimulation command code appearing at terminals 13, 14, 15, 16, 4, 5, 6 and 7 of D/A converter 13. The output of D/A converter 14 is buffered and amplified and thereafter applied to input line 197 of stimulator 50.

Computer 13 generates eight-bit binary representation of stimulation command voltages ranging between 0 and 255 by executing an appropriate POKE instruction. A desired stimulation voltage ranging between 0 and 255 is POKED into memory location 50016 (decimal). When this memory location is POKED the computer generates an address for IC201 which causes output pin 12 to go LO. This LO output signal is inverted by inverter 205 to create the above mentioned strobe signal for D/A converter 14.

The computer program for producing the above described operation is described in the program listing set forth in TABLE IV. This program is written in source code in accordance with the APPLESOFT variation of the well known BASIC language. The program will be self-explanatory to persons skilled in the art and only brief comments need be made.

The program set forth in TABLE IV includes an isometric strength measurement routine beginning at line 220 and a main control program beginning at line 1000. The main control program includes a start cycle beginning at line 1250 and a muscle stimulation routine beginning at line 1432. The start cycle finds the beginning of a ramp generated by the profile generator 202.

During the isometric measurement routine the computer increments a variable Y from 1 to 17 (line 290) and POKES the value 10Y into memory location 50016. This causes generation of stimulation pulses having a voltage equal to the value 10Y. When the muscle begins to develop tension, then the test supervisor depresses the Escape key on the computer control board. This action loads the ASCII code 155 into memory location 49152. The computer checks that memory location at line 329 and jumps to line 400 if the Escape key has been depressed. The computer then assigns the current value 10Y to the variable Z as a threshold voltage.

After the threshold voltage has been established, the computer enters the main control program to determine the maximum strength of the muscle by isokinetic exercise. During this routine the computer steps the stimulation voltage from the value Z up to 255 volts in 10 volt steps (lines 1045 and 1060). During this period of time the leg is attached to cable 34 as indicated by FIG. 3. When strength meter 36 indicates that the strength has leveled off, then the test supervisor again depresses the Escape key. The computer checks memory location 49152 once during each voltage step (line 1105) and proceeds to line 1120, if the Escape key has been depressed.

After the maximum strength has been determined, the computer looks for a start of a cycle (line 1250).

The isokinetic exercise routine begins at line 1432. During this routine the computer generates stepped variations for a variable Z9 and POKES the value of Z9 into memory location 50016. After each new value of Z9 has been utilized for generation of a corresponding stimulation voltage, the computer checks to see if Z9 has a value equal to 255 (maximum stimulation voltage). If that value is noted, than the isokinetic exercise routine is terminated. If not, the computer proceeds to execute the instructions at line 1450 which cause reading of the analog voltages generated by profile generator 202 and potentiometer 17. These voltages are digitized and utilized to establish values for variables A8 and A9 respectively.

If A8 is greater than A9, the computer knows that the leg is not raised as much as it should be, and the value of Z9 is increased. This then increases the stimulation voltage command generated by the computer. Conversely, if A8 is less than A9, Z9 and the stimulation command are decreased. When A8 has decreased to a value indicating the end of a cycle, then the leg is rested for the duration of a counting loop which continues for approximately 6 seconds.

A complete exercise procedure is therefore seen to include the following steps:

(1) Apply electrodes to subject.
(2) Turn on computer 13.
(3) Hook leg strap 19 to strength testing cable 34.
(4) Secure leg strap 19 to leg of subject.
(5) Connect electrical lead to electrode 15a, 15b and 15c with the HV ground line being connected to electrode 15c.
(6) Input "GO" into computer, thereby causing the computer to generate signals for application of stimulation voltages to electrode pairs 15a-15c and 15b-15c; the steps being in 10 volt increments from 10 volts to 170 volts max.
(7) Look for muscle contraction. When muscle contraction is noted, depress Escape key on computer, thereby causing the computer to store the threshold voltage.
(8) Determine muscle strength by typing "GO" into computer, thereby causing the computer to generate commands for production of stimulation voltages in 10 volt steps from the threshold voltage to a maximum of 255 volts.
(9) Observe strength meter. When strength has leveled off, depress Escape key on computer keyboard, thereby discontinuing the application of stimulation signals to the subject.
(10) Attach leg strap 19 to dynamic exercise cable 33.
(11) Place weights 27 on weight pan 42. The weight of the load should be some predetermined fraction of the maximum strength as determined above, typically one-third or two-thirds.
(12) Initiate isokinetic exercise by typing "GO" into computer. This command causes generation of a stimulation voltage profile as illustrated in FIGS. 7 and 8. The leg reacts to this voltage profile by repeated cycles of raising, lowering and resting.
(13) When the exercise routine is completed (assuming that the muscle has not become exhausted and caused automatic shutdown) discontinue the routine by turning off the computer.

While the method herein described and the form of apparatus for carrying this method into effect constitutes preferred embodiments of this invention, it is to be understood that the invention is not limited to this precise method and form of apparatus, and that changes may be made in either without departing from the scope of the invention which is defined in the appended claims.

TABLE IV

| | |
|---|---|
| 1 | POKE 50016,10 |
| 2 | REM Z=THRESHOLD VOLTAGE |
| 3 | REM STRENGTH=MAXIMUM VOLTAGE LEVEL |
| 4 | REM K3=LOW GAIN CAL . . . K2=HIGH GAIN CAL |
| 5 | REM G3=REAL STRENGTH |
| 6 | K3 = .05:K2 = 1 / 46 |
| 7 | DIM A(1000) |
| 10 | REM ********************************* |
| 20 | REM EXERCISE 1 PROGRAMS |
| 30 | REM ********************************* |
| 40 | REM |
| 50 | REM |
| 51 | POKE 50016,10 |
| 100 | FOR X = 1 TO 30: PRINT : NEXT X |
| 110 | PRINT "THIS PROGRAM STIMULATES": PRINT "THE QUADRICEPS MUSCLE" |
| 120 | PRINT : PRINT : PRINT |
| 125 | PRINT "SET UP DYNAMOMETER FOR ISOMETRICS": PRINT : PRINT |
| 130 | PRINT "CONNECT LEADS TO SUBJECT NOW" |
| 140 | PRINT : PRINT "BLACK LEAD TO CENTER" |
| 150 | PRINT |
| 160 | PRINT "TYPE GO OR WHEN READY" |
| 170 | INPUT A$ |
| 180 | IF A$ = "GO" THEN 200 |
| 190 | GOTO 160 |
| 200 | PRINT : PRINT : PRINT : PRINT : PRINT : PRINT : PRINT |
| 210 | FOR I = 1 TO 25: PRINT : NEXT I |
| 220 | PRINT "MEASUREMENT OF ISOMETRIC STRENGTH" |
| 230 | PRINT : PRINT : PRINT |
| 240 | PRINT "DEFINE THRESHOLD": PRINT |
| 250 | PRINT "TO DETERMINE THE THRESHOLD": PRINT "WATCH THE MUSCLE AND NOTE": PRINT "WHEN THE MUSCLE STARTS TO ": PRINT "CONTRACT" |
| 260 | PRINT "TYPE ESC WHEN THE MUSCLE DEVELOPS": PRINT "TENSION" |
| 270 | PRINT : PRINT "THRESHOLD WILL BE PRINTED": PRINT "AT THE END" |
| 271 | PRINT : PRINT "SET DYNAMOMETER TO ZERO": PRINT "TURN ON STIMULATOR" |
| 275 | PRINT : PRINT : FLASH : PRINT "CONTROL C TO STOP AND SWITCH": NORMAL |
| 280 | PRINT : PRINT "TYPE ANY KEY TO START": INPUT S$ |
| 283 | PRINT : PRINT : FLASH |

TABLE IV-continued

| | |
|---|---|
| 284 | NORMAL |
| 285 | FOR H = 1 TO 300:U = SIN (H): NEXT H |
| 290 | FOR Y = 1 TO 17 |
| 295 | PRINT "VOLTAGE LEVEL=";Y * 10 |
| 300 | FOR I = 1 TO 150 |
| 310 | POKE 50016,Y * 10 |
| 320 | NEXT I |
| 325 | POKE 50016,10: FOR H = 1 TO 300: NEXT H |
| 329 | G1 = PEEK (49152): IF G1 = 155 THEN GOTO 400 |
| 330 | NEXT Y |
| 400 | Z = Y * 10 − 10: PRINT : PRINT "THRESHOLD WAS ";Y * 10 |
| 401 | POKE 49168,0 |
| 410 | FOR X = 1 TO 1000: NEXT X |
| 411 | FOR X = 1 TO 3000: NEXT X |
| 500 | FOR H = 1 TO 700: NEXT H |
| 550 | FOR I = 1 TO 30: PRINT : NEXT I |
| 599 | INVERSE : PRINT "ISOKINETIC EXERCISE" |
| 600 | REM |
| 601 | NORMAL |
| 610 | FOR I = 1 TO 10: PRINT : NEXT I |
| 620 | FOR I = 1 TO 700: NEXT I |
| 621 | FOR I = 1 TO 2000: NEXT I |
| 699 | GOTO 1000: REM ***RE ACTIVATE FOR VARIABLE SPEED CONTRACTIONS BY REMOVING THIS LINE***************** |
| 700 | PRINT "WHAT VELOCITY DO YOU WANT" |
| 710 | PRINT : PRINT : PRINT |
| 720 | PRINT "ENTER S FOR SLOW AND F FOR FAST": PRINT : PRINT : PRINT |
| 730 | INPUT D$ |
| 740 | IF D$ = "S" THEN GOTO 800 |
| 750 | IF D$ = "F" THEN GOTO 900 |
| 760 | PRINT "NON LEGAL INPUT . . . TRY AGAIN": GOTO 710 |
| 800 | REM START SLOW ROUTINES |
| 805 | R = 3 |
| 810 | LET VEL = R |
| 850 | GOTO 1000 |
| 900 | REM START FAST ROUTINES |
| 905 | R = 50 |
| 910 | LET VEL = R |
| 950 | GOTO 1000 |
| 1000 | REM MAIN CONTROL PROGRAM |
| 1010 | POKE 50016,10 |
| 1020 | REM DETERMINE STRENGTH |
| 1030 | FOR I = 1 TO 10: PRINT : NEXT I |
| 1040 | PRINT "DETERMINE MAXIMUM STRENGTH OF MUSCLE": PRINT : PRINT : PRINT |
| 1041 | PRINT "WHEN STRENGTH HAS LEVELED OFF": PRINT "TYPE ESC": PRINT : PRINT : FLASH : PRINT "CONTROL C AND SWITCH TO STOP FAST": NORMAL : PRINT |
| 1043 | PRINT : PRINT "TYPE GO TO START": INPUT A$: IF A$ = "GO" THEN GOTO 1044: GOTO 1043 |
| 1044 | REM |
| 1045 | FOR J = Z TO 255 STEP 10 |
| 1046 | PRINT "VOLTAGE LEVEL =";J |
| 1050 | FOR I = 1 TO 100 |
| 1060 | POKE 50016,J |
| 1070 | REM |
| 1080 | NEXT I |
| 1090 | POKE 50016,10 |
| 1100 | FOR U = 1 TO 2000: NEXT U |
| 1105 | G1 = PEEK (49152): IF G1 = 155 THEN GOTO 1120 |
| 1110 | NEXT J |
| 1120 | PRINT : PRINT : PRINT "VOLTAGE LEVEL AT MVC=";J: PRINT : PRINT |
| 1121 | POKE 49168,0 |
| 1130 | STRENGTH = J |
| 1140 | REM STRENGTH = VOLTAGE LEVEL AT MVC |
| 1145 | POKE 49168,0 |
| 1146 | PRINT "WHAT IS THE READING?": INPUT METER: PRINT "INPUT THE GAIN . . . 1 FOR HIGH . . . 2 FOR LOW": INPUT GAIN |
| 1147 | REM |
| 1148 | GOTO 8000 |
| 1149 | FOR I = 1 TO 10: PRINT : NEXT I: GOSUB 5000 |
| 1150 | FOR I = 1 TO 30: PRINT : NEXT I |
| 1155 | FOR I = 1 TO 30: PRINT : NEXT I |
| 1156 | D$ = "" |
| 1157 | PRINT D$; "RUN STIM" |

TABLE IV-continued

```
1160    PRINT "SET UP DYNAMOMETER FOR DYNAMIC"
1170    PRINT "EXERCISE"
1180    NORMAL
1190    FOR I = 1 TO 10: PRINT : NEXT I
1200    REM
1220    PRINT "TYPE GO TO CONTINUE"
1230    INPUT A$
1240    IF A$ = "GO" THEN GOTO 1250: GOTO 1220
1250    REM LOOK FOR START OF CYCLE
1255    D9 = 0
1260    FOR X = 1 TO 1000
1265    POKE 50080,0
1270    A(X) = PEEK (49952)
1280    NEXT X
1290    G7 = 150
1300    FOR X = 1 TO 1000
1310    IF G7 > A(X) THEN G7 = A(X)
1320    NEXT X
1330    POKE 50080,0
1340    G8 = PEEK (49952)
1350    IF G8 < G7 + 5 THEN GOTO 1400
1360    GOTO 1330
1400    REM STIMULATE THE LEG
1405    FLASH : PRINT "TURN OFF POWER THEN CONTROL C
        TO END": NORMAL
1410    PRINT "CONTRACTION ";D9 + 1:D9 = D9 + 1
1420    REM
1430    FOR X = 1 TO 250: NEXT X
1432    REM ********STIMULATE MUSCLE*****
1435    Z9 = Z
1440    POKE 50016,Z9
1441    IF Z9 = 255 THEN GOTO 6000
1450    POKE 50080,0:A8 = PEEK (49952): POKE
        50082,0:A9 = PEEK (49952)
1460    IF A8 > A9 THEN LET Z9 = Z9 + 1
1470    IF A8 < A9 THEN LET Z9 = Z9 - 1 1
1480    IF A8 < G7 + 3 THEN GOTO 1500
1490    GOTO 1440
1500    POKE 50016,2
1510    FOR I = 1 TO 1000: NEXT I
1520    GOTO 1330
1530    REM
1540    REM
1550    REM
5000    REM *************************
5010    REM THIS SUBROUTINE LISTS STRENGTH AND LOAD
5020    REM *************************
5030    REM
5040    PRINT : PRINT "WHAT TYPE OF EXPERIMENT?"
5041    PRINT "(1) FOR NO LOAD"
5042    PRINT "(2) FOR 33% LOAD"
5043    PRINT"(3) FOR 66% LOAD"
5044    PRINT
5050    INPUT TYPE
5055    IF TYPE > 4 THEN GOTO 5040
5056    IF TYPE = 0 THEN GOTO 5040
5057    IF TYPE = 4 THEN GOTO 5040
5060    IF GAIN = 1 THEN GOTO 5100
5070    IF GAIN = 2 THEN GOTO 5200
5080    GOTO 1145
5100    G3 = K2 * METER
5110    GOTO 5500
5200    G3 = K3 * METER
5210    GOTO 5500
5500    PRINT "THE STRENGTH WAS ";G3;"POUNDS"
5510    PRINT
5520    IF TYPE = 1 THEN GOTO 5600
5530    IF TYPE = 2 THEN GOTO 5700
5540    IF TYPE = 3 THEN GOTO 5800
5550    GOTO 1145
5600    PRINT "SET THE LOAD TO NO WEIGHT . . . ": PRINT :
        PRINT "THIS IS A ZERO LOAD EXPERIMENT"
5610    GOTO 5900
5700    PRINT "THE LOAD MUST BE SET AT ";G3 / 3;"LBS"
5710    GOTO 5900
5800    PRINT "THE LOAD MUST BE SET AT ";2 * G3 /3;"
        LBS": PRINT : PRINT : PRINT: PRINT : FLASH :
        PRINT "SO . . . SET IT": NORMAL
5810    GOTO 5900
5900    FOR I = 1 TO 300:H = SIN (54): NEXT I
5910    RETURN
6000    REM *END PROGRAM DUE TO FATIGUE*
```

TABLE IV-continued

| | |
|---|---|
| 6005 | POKE 50016,2 |
| 6010 | PRINT : PRINT : PRINT : PRINT : PRINT : PRINT |
| 6020 | PRINT "THE MUSCLE IS BEING STIMULATED FULLY": PRINT "EITHER THE MUSCLE IS FATIGUED OR": PRINT "SOMETHING IS WRONG . . . END PROGRAM" |
| 6025 | PRINT "TYPE " CONT " TO RESUME OR THE PROGRAM ENDS" |
| 6026 | INPUT A$: IF A$ = "CONT" THEN GOTO 1330 |
| 6030 | END |
| 8000 | REM CHECK FOR BAD ENTRY |
| 8010 | IF METER = 0 THEN GOTO 1146 |
| 8020 | IF METER > 1000 THEN GOTO 1146 |
| 8030 | IF GAIN = 0 THEN GOTO 1146 |
| 8040 | IF GAIN > 2.1 THEN GOTO 1146 |
| 8050 | GOTO 1149 |

What is claimed is:

1. Method of exercising a human muscle comprising the steps of:
   (1) attaching a plurality of transcutaneous stimulators to the skin of said human in a pattern above said muscle,
   (2) applying to said stimulators a plurality of stimulation signals having profiles for causing said muscle to contract and produce movement of a limb connected thereto,
   (3) applying a resisting force to said limb for causing exertion of said muscle during said movement,
   (4) sensing said movement and generating a feedback signal corresponding thereto,
   (5) monitoring said feedback signal to determine when a predetermined response has been achieved,
   (6) after said predetermined response has been achieved, altering said stimulation and permitting said muscle to relax, and
   (7) repeating aforesaid steps to produce an exercise routine.

2. Exercising method comprising the steps of:
   (1) attaching a plurality of transcutaneous stimulation electrodes to an area of skin in a pattern for selectively stimulating at least one muscle thereunder,
   (2) restraining movement of a limb connected for movement by said muscle,
   (3) applying a series of increasingly severe isometric stimulation signals to said stimulation electrodes,
   (4) measuring the movement force developed by said limb during stimulation by said isometric stimulation signals,
   (5) recording the maximum straining force developed by said limb during isometric stimulation thereof,
   (6) discontinuing said isometric stimulation signals,
   (7) freeing said limb for movement,
   (8) applying a series of dynamic stimulation signals to said stimulation electrodes for initiating movement of said limb,
   (9) applying against said limb a movement resisting force having a magnitude which is a predetermined fraction of said maximum straining force,
   (10) sensing movement of said limb and generating a feedback signal corresponding thereto,
   (11) adjusting said stimulation signals in response to said feedback signal for controlling the motion of said limb in a predetermined manner,
   (12) interrupting said dynamic stimulation signals to permit said muscle to relax, and
   (13) repeating aforesaid steps 8-12 to produce an exercise sequence.

3. Method according to claim 2 and further comprising the step of discontinuing said exercise routine when said feedback signal causes said dynamic stimulation signals to reach a level indicating muscle fatigue.

4. Method according to claim 3 and further comprising the steps of recording the isometric stimulation signal level which first produces muscular response and setting the initial value of said dynamic stimulation signals equal to said isometric stimulation signal level.

5. Method according to any of claims 1-4 wherein said stimulation signals are pulsed.

6. Method according to claim 5 wherein said stimulation signals are applied across said electrodes in two pairs; the signal across each said electrode pair being pulsed at frequency between about 55 and 65 Hz and the pulses across different electrode pairs being alternated.

7. Method according to claim 6 wherein said pulses have a duration of about 500 microseconds.

8. Apparatus for exercising a paralyzed leg comprising:
   a chair including a seat,
   a leg strap retained below said seat for grasping said leg,
   cable means for connection to said strap,
   load means for applying a leg restraining tension to said cable means,
   feedback means for generating a feedback signal corresponding to movement of said cable means, and
   stimulation means responsive to said feedback signal for stimulating normally paralyzed muscles within said leg to cause coordinated movement thereof against the restraining action of said load means.

9. Apparatus according to claim 8 and further comprising releasible restraining means for restraining movement of said strap and force indicating means for providing an indication of the force exerted by said leg against said strap when said muscle is stimulated and said strap is restrained as aforesaid.

10. Apparatus according to claim 8 wherein said load means comprises vertical support means for suspending a plurality of selected weights and means for transmitting the combined weight force of said weights into said cable means.

11. Apparatus according to claim 10 wherein said feedback means comprises a potentiometer mounted for activation by movement of said cable means.

12. Apparatus according to any of claims 8-11 wherein said chair is movable relative to said strap for permitting attachment of said strap to either leg of a person seated in said chair.

* * * * *

UNITED STATES PATENT AND TRADEMARK OFFICE
CERTIFICATE OF CORRECTION

PATENT NO. : 4,480,830
DATED : November 6, 1984
INVENTOR(S) : Jerrold S. Petrofsky et al It is certified that error appears in the above-identified patent and that said Letters Patent is hereby corrected as shown below:

Column 2, line 36, "minics" should be --mimics--.

Column 6, line 53, Table III, "R/W" should be --R/$\overline{W}$--.

Column 6, line 54, Table III, "Write" should be --$\overline{\overline{Write}}$--.

Column 7, line 23, Table III, "CS" should be --$\overline{CS}$--.

Column 7, line 24, Table III, "WR$_1$", should be --$\overline{WR}_1$--.

Column 15, line 1470, Table IV, "Z9-11" should be --Z9-1--.

Signed and Sealed this

Fourth Day of June 1985

[SEAL]

Attest:

DONALD J. QUIGG

Attesting Officer     Acting Commissioner of Patents and Trademarks